(12) United States Patent
Hildebrandt et al.

(10) Patent No.: US 7,043,968 B1
(45) Date of Patent: May 16, 2006

(54) DIRECTLY REFRIGERATED BLOCK

(75) Inventors: Marc J. Hildebrandt, Midland, MI (US); Theodore W. Selby, Midland, MI (US)

(73) Assignee: King Refrigeration, Inc., Freeland, MI (US)

( * ) Notice: Subject to any disclaimer, the term of this patent is extended or adjusted under 35 U.S.C. 154(b) by 57 days.

(21) Appl. No.: 10/674,168

(22) Filed: Sep. 29, 2003

(51) Int. Cl.
*G01N 11/14* (2006.01)

(52) U.S. Cl. .................................... 73/54.28

(58) Field of Classification Search .............. 73/54.28, 73/54.29, 54.31, 54.32, 54.33, 54.34, 54.35; 165/174, 179; 436/37
See application file for complete search history.

(56) References Cited

U.S. PATENT DOCUMENTS

| | | | | |
|---|---|---|---|---|
| 2,318,206 | A | * 5/1943 | Eisenlohr ...................... | 138/37 |
| 4,272,907 | A | * 6/1981 | Skapura ........................ | 43/92 |
| 4,472,963 | A | 9/1984 | Gyer et al. .................... | 73/60 |
| 4,534,409 | A | * 8/1985 | Cadars ..................... | 165/109.1 |
| 4,784,218 | A | * 11/1988 | Holl ........................ | 165/109.1 |
| 4,993,485 | A | * 2/1991 | Gorman ....................... | 165/85 |
| 5,167,275 | A | * 12/1992 | Stokes et al. ............. | 165/109.1 |
| 5,604,300 | A | * 2/1997 | Sayers et al. ............... | 73/54.31 |
| 5,821,407 | A | * 10/1998 | Sekiguchi et al. ......... | 73/54.28 |
| 5,852,230 | A | 12/1998 | Selby et al. ................ | 73/54.35 |
| 5,877,410 | A | 3/1999 | Duke ........................ | 73/54.28 |
| 6,306,658 | B1 * | 10/2001 | Turner et al. ................. | 436/37 |
| 6,786,081 | B1 | 9/2004 | Hildebrandt et al. ....... | 73/54.43 |

OTHER PUBLICATIONS

ASTM D 4684-98.
CANNON® Mini-Rotary Viscometer, Catalog pp. 47-49.
Hildebrandt, "A New Direct Refrigeration Approach to MRV/TP1," Unpublished Draft, Apr. 25, 2003 A.D.
Hildebrandt et al., "A New Direct Refrigeration Approach to MRV/TP1 Low Temperature Pumpability . . . , " Review Version, Oct. 22, 2002 San Diego.
Hildebrandt et al., U.S. Appl. No. 10/077,236, filed Feb. 15, 2002.
Hildebrandt et al., U.S. Appl. No. 60/269,372, filed Feb. 16, 2001.
Hildebrandt et al., U.S. Appl. No. 60/310,768, filed Aug. 8, 2001.
Reese, Chem. & Eng. News, Newscripts,"Odd Device may be the Work of Maxwell's Demon," p. 56, Mar. 11, 1996 A.D.

* cited by examiner

*Primary Examiner*—Charles Garber
(74) *Attorney, Agent, or Firm*—Christopher John Rudy

(57) ABSTRACT

Directly refrigerated component or system in which a refrigerating pathway is provided with passive cooling moderation. The passive cooling moderation can be provided, for example, by a passive cooling moderator that has moderating live space, or by a passive cooling moderator has moderating dead space. The component or system can be a test device for rotational viscometric testing of an oleaginous fluid, and, when it has test wells and sample sleeves which go into the wells, the sample sleeves can be stopped from rotating in the wells by a pin and pin-engaging hole or slot arrangement.

10 Claims, 6 Drawing Sheets

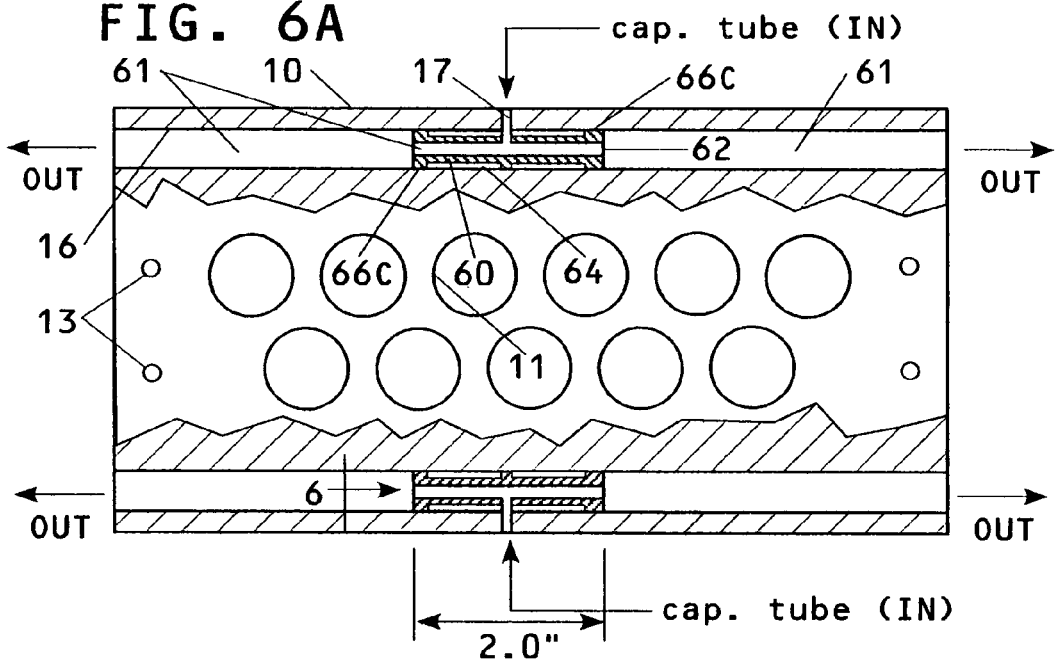
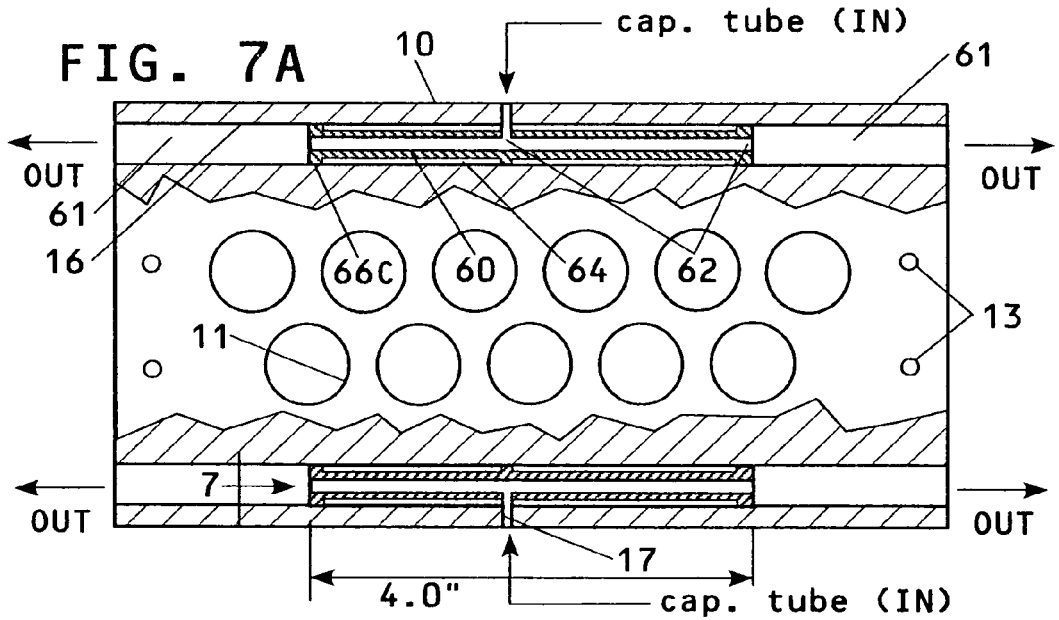

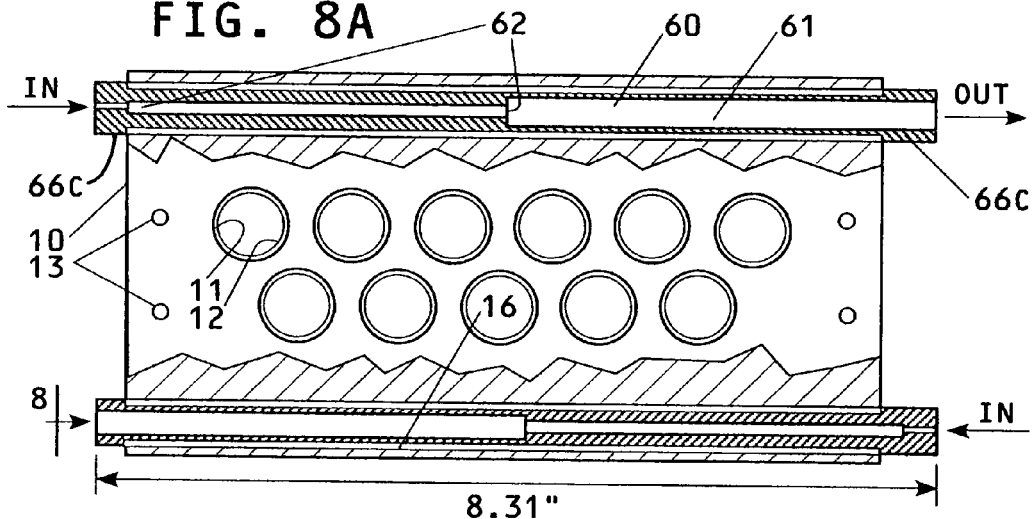
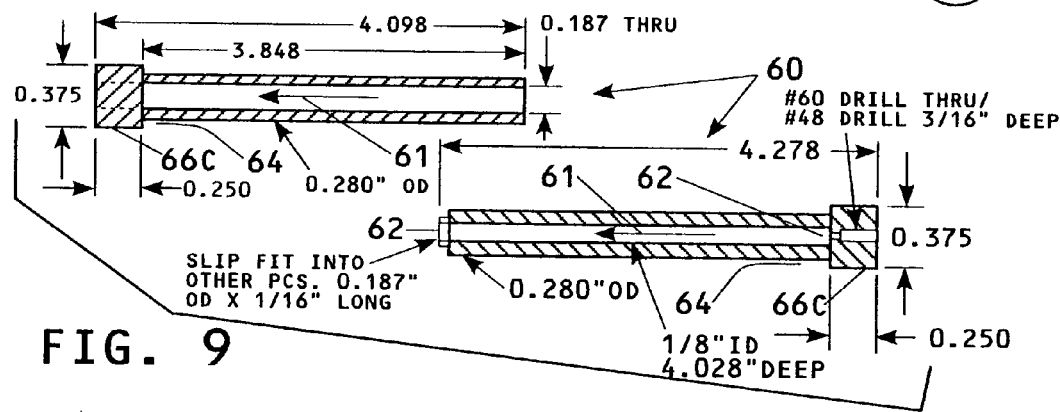
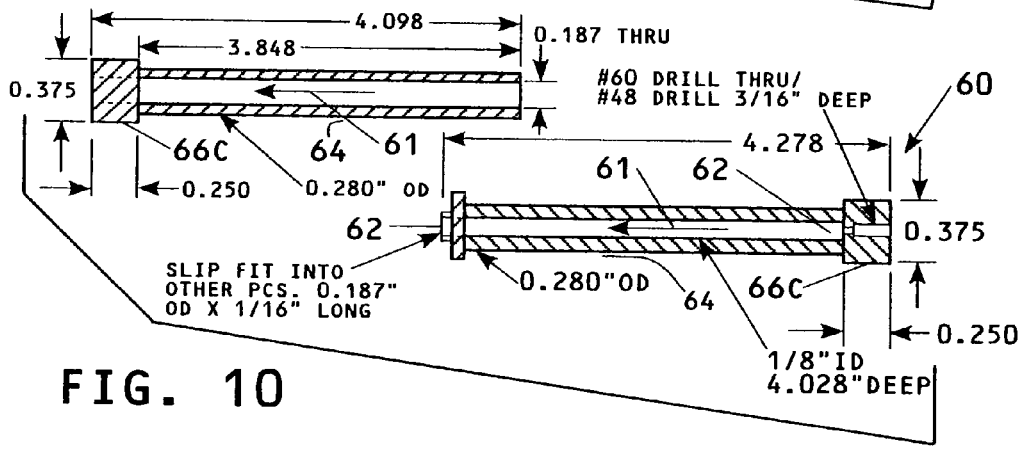

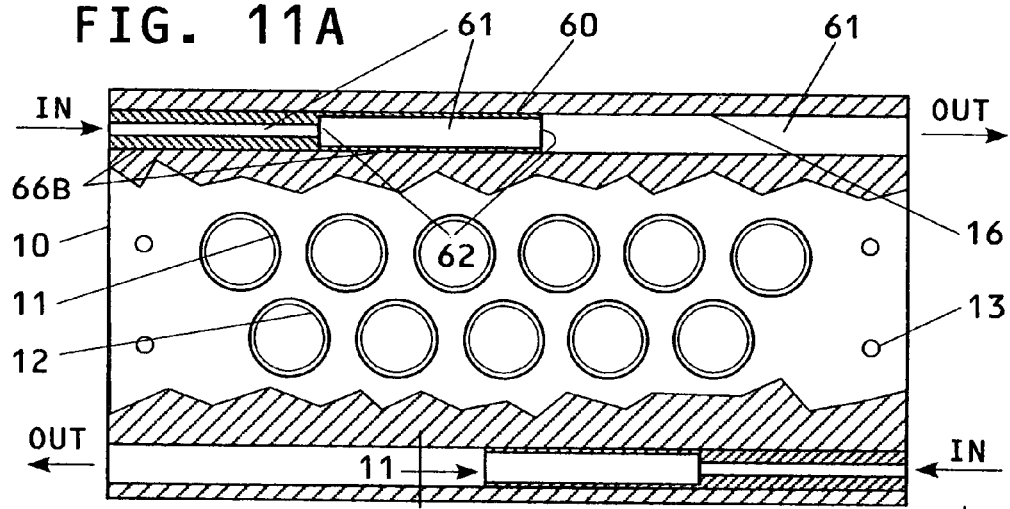
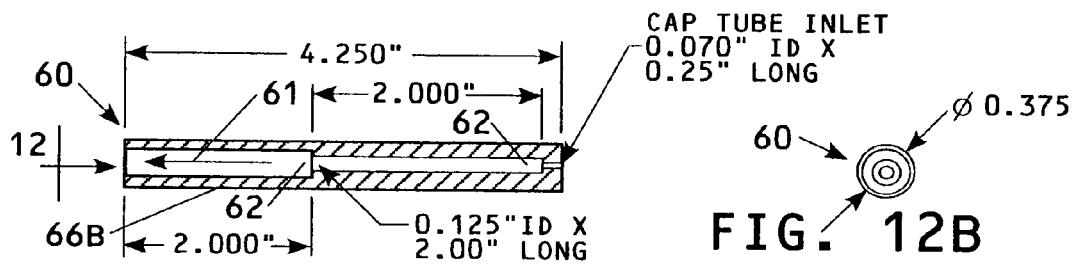
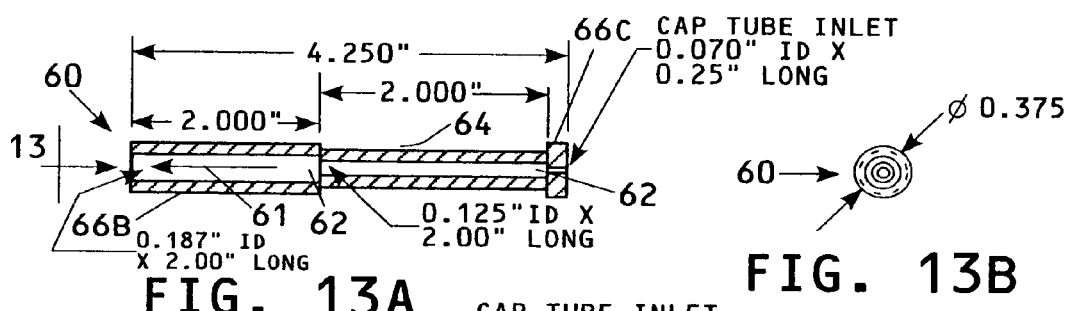
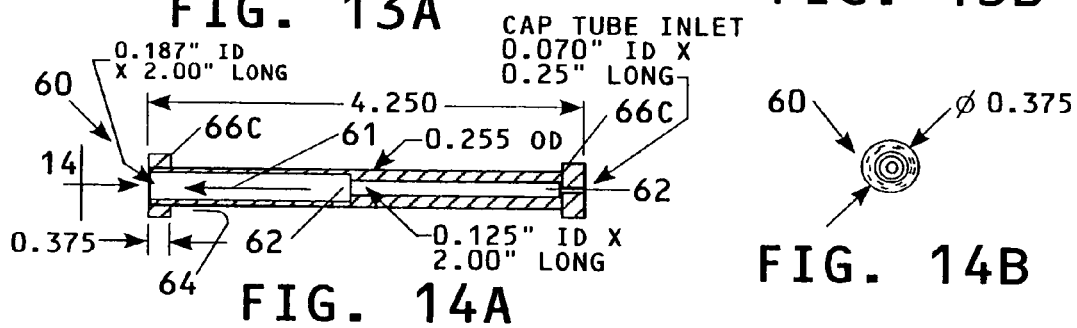

DIRECTLY REFRIGERATED BLOCK

BACKGROUND TO THE INVENTION

I. Field and Purview

The present invention concerns a device for direct refrigeration of a component of a system or the entire system by which a cooling intermediary such as methanol or other liquid can be avoided and in which expansion of refrigerant in the component or system itself cools, directly, the same. Typically, heating is carried out. The foregoing can be carried out, in particular, with a solid heat-conductive block, for example, a metal block in which sample test cell(s) is(are) present such as for viscometric testing of an engine oil and so forth at a specified temperature. Among other things, the invention provides for cooling moderation so as to ameliorate or avoid perceptible cold spots in the block.

II. Art and Problems

Hildebrandt et al., U.S. patent application Ser. No. 10/077,236 filed on Feb. 15, 2002 A.D., which issued as U.S. Pat. No. 6,786,081 (Sep. 7, 2004), discloses direct and/or opposing flowpath refrigeration. In a particular case, that invention is embodied to include a block having test cells for viscometric testing of oil, which can be beneficially employed in ASTM D 4684 type testing, and supplant the Cannon Mini-Rotary Viscometer (MRV). Compare, Selby et al., U.S. Pat. No. 5,852,230.

As fine an instrument as is the device of Hildebrandt et al., it is not without its drawbacks. Chief among these are that, although laboratory safety owing to the absence of methanol and control of temperature are excellent and better than those of the MRV, in the rapidly evolving field of oil testing, where advances in data collection and interpretation follow upon instrumental precision, the temperature may vary slightly from cell to cell with a perceptible cold spot appearing, particularly about the location at which the refrigerant supply enters the block; and control of the temperature was not as symmetrical as sought, and the bar is high, with respect to a rectangular box shaped block.

It would be desirable to ameliorate or overcome the same.

FURTHER DISCLOSURE OF THE INVENTION

In general, the invention provides, in one aspect, a directly refrigerated component or system in which a refrigerating pathway is provided with passive cooling moderation. In another aspect, use of such device is provided.

The invention is useful in refrigeration and in oil testing.

Significantly, by the invention, one or more problems in the art are ameliorated if not overcome. In particular, tempering of the cooling is provided passively, and cold spot temperature disparities are greatly reduced. With such tempering, control of temperature throughout a block can be most precise, for example, an array of test cells in a rectangular box metal block, which has auxiliary heaters, at least about ±0.2 degrees C., and this in a more asymmetric fashion with respect to the block. Moreover, particular embodiments of the auxiliary heater subsystem provided hereby can assist in the quite literally astounding control of temperature provided hereby.

Numerous further advantages attend the invention.

The drawings form part of the present specification. With respect to the drawings, which are not necessarily drawn to scale, the following is briefly noted:

FIG. 6 shows another embodiment hereof, having a directly refrigerated block with passive cooling moderation, and focusing upon its passive cooling moderators, also of a center-feed variety, as a top view in part section (A); and a view of a passive cooling moderator whereof, taken along arrow 6 (B).

FIG. 7 shows another embodiment hereof, having a directly refrigerated block with passive cooling moderation, and focusing upon its passive cooling moderators, also of a center-feed variety, as a top view in part section (A); and a view of a passive cooling moderator whereof, taken along arrow 7 (B).

FIG. 8 shows another embodiment hereof, having a directly refrigerated block with passive cooling moderation, and focusing upon its passive cooling moderators, which are of an end-feed variety, as a top view in part section (A); and a view of a passive cooling moderator whereof, taken along arrow 8 (B).

FIGS. 9 and 10 are sectional views of other end-feed variety passive cooling moderators, which, as found in FIG. 9, extend across the length of the block, but which are formed in separate sections for assembly. These, too, are radially symmetrical.

FIG. 11 shows another embodiment hereof, having a directly refrigerated block with passive cooling moderation, and focusing upon its passive cooling moderators, also of an end-feed variety, as a top view in part section (A); and a view of a passive cooling moderator whereof, taken along arrow 11 (B).

Figure 1A:
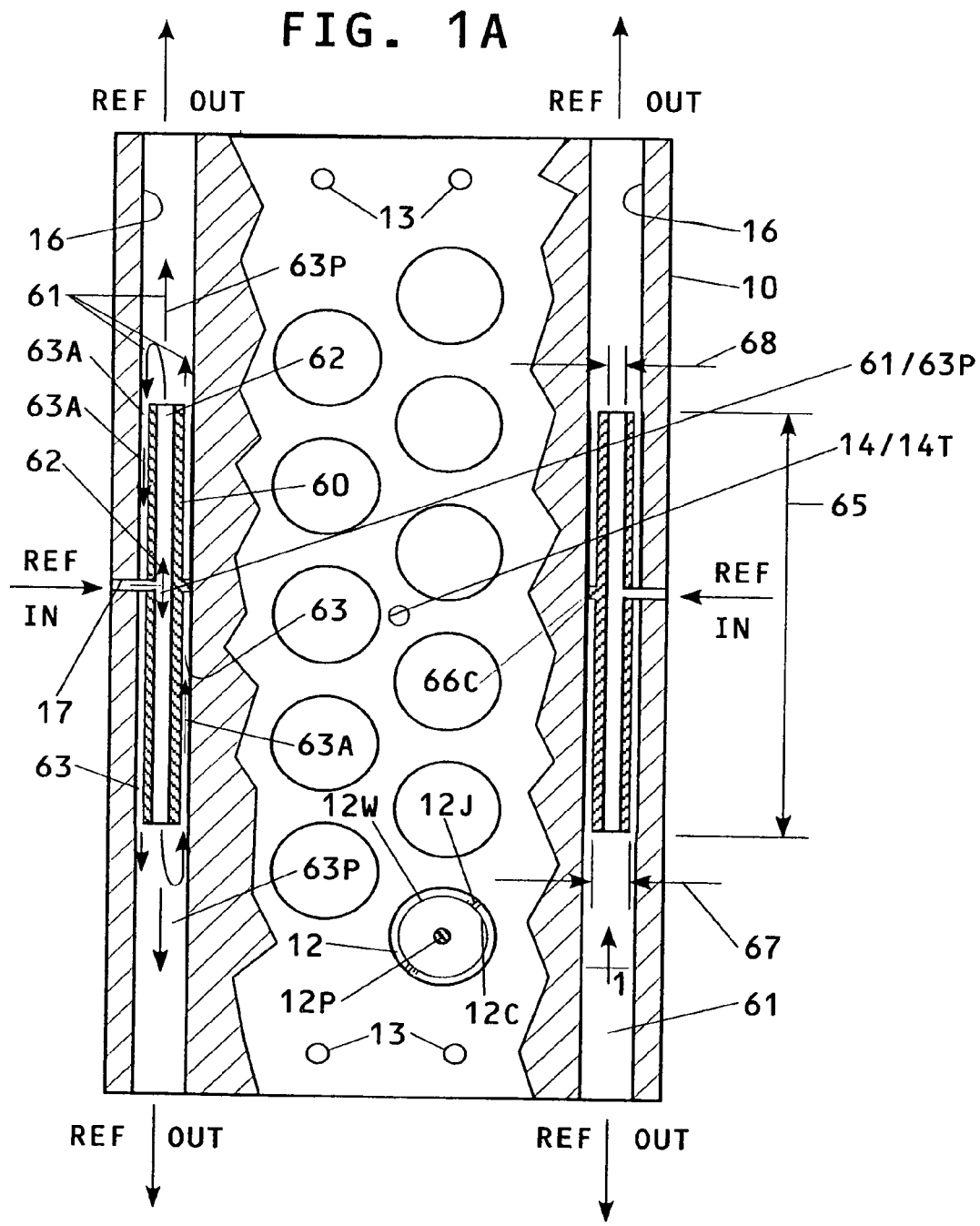
FIG. 1 shows plan views of a device of the invention, embodied with a directly refrigerated block having passive cooling moderation, focusing upon its passive cooling moderators, which are of a center-feed variety, as a top view in part section (A); and a view of a passive cooling moderator whereof, taken along arrow 1 (B).
Figure 1B:
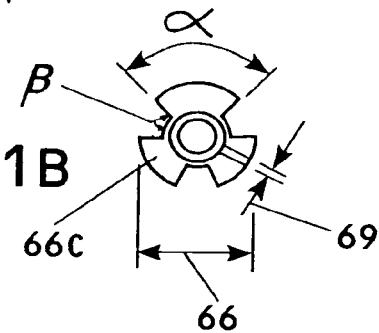
Figure 2:
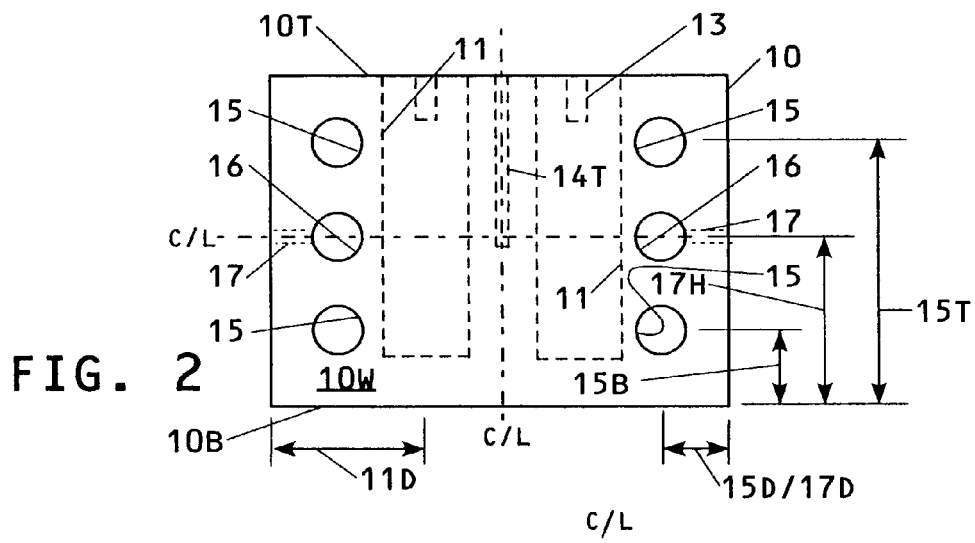
FIG. 2 is an end view of a block as of FIG. 1, in general, with its passive cooling moderators absent.
Figure 3:
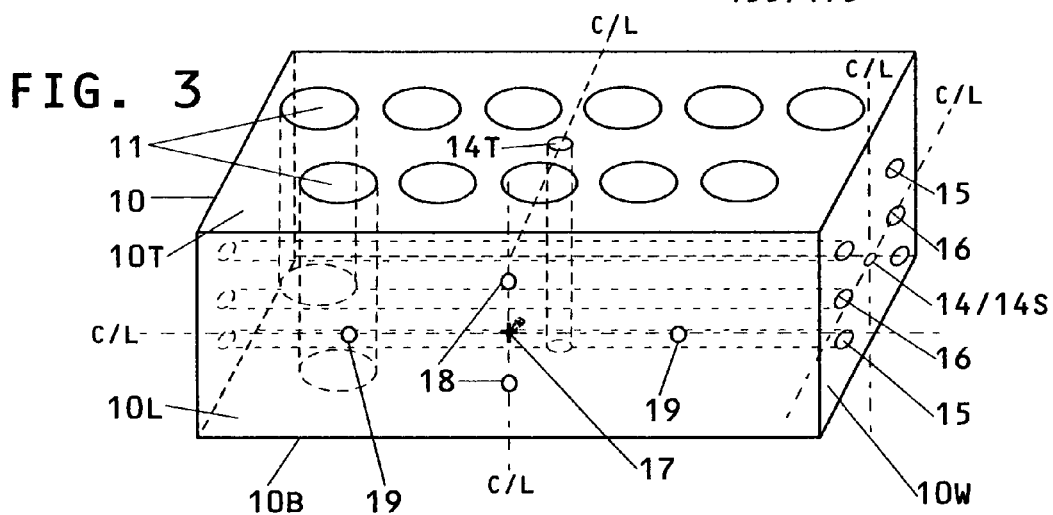
FIG. 3 is a perspective plan view of a block as of FIG. 1.
Figure 4:
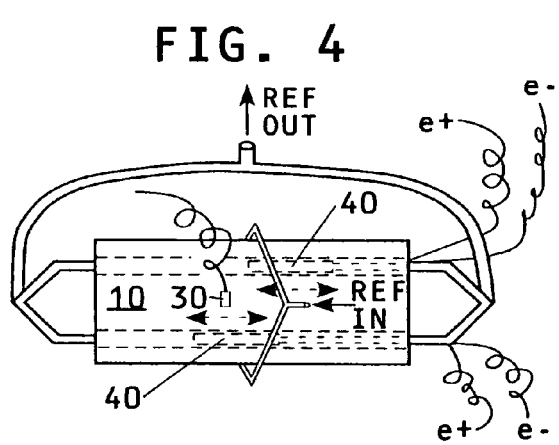
FIG. 4 is top plan view of a block as of FIG. 1, focusing upon its refrigerant delivery and auxiliary heating systems.

FIGS. 12–14 are views of other end-feed, passive cooling moderators, each also employable in blocks as of FIG. 1 et seq., 6–8 and 11, as sectional views (A); and views of each passive cooling moderator whereof, taken, respectively, along arrows 12, 13 and 14 (B).

Figure 15:
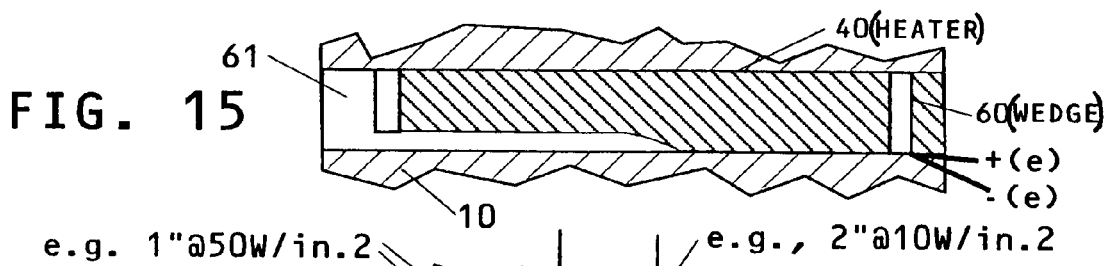

FIG. 15 is a side plan view of another embodiment hereof, having a directly refrigerated block with passive cooling moderation, which employs variable watt density heaters.

Figure 16:
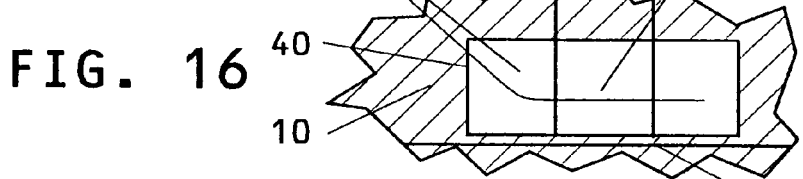

FIG. 16 is a side plan view of another embodiment hereof, having a directly refrigerated block with passive cooling moderation, with a heater around the passive cooling moderator.

Figure 5:
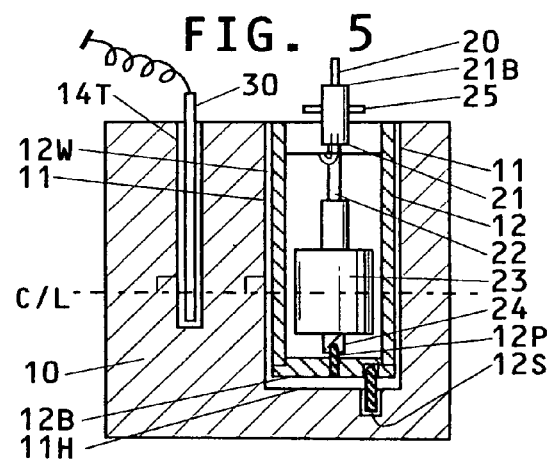
FIG. 5 is a front plan view of parts found in the block of FIG. 1, focusing upon temperature probe and rotor positioning when the block is employed in viscometric/rheologic testing.
Figure 17A:
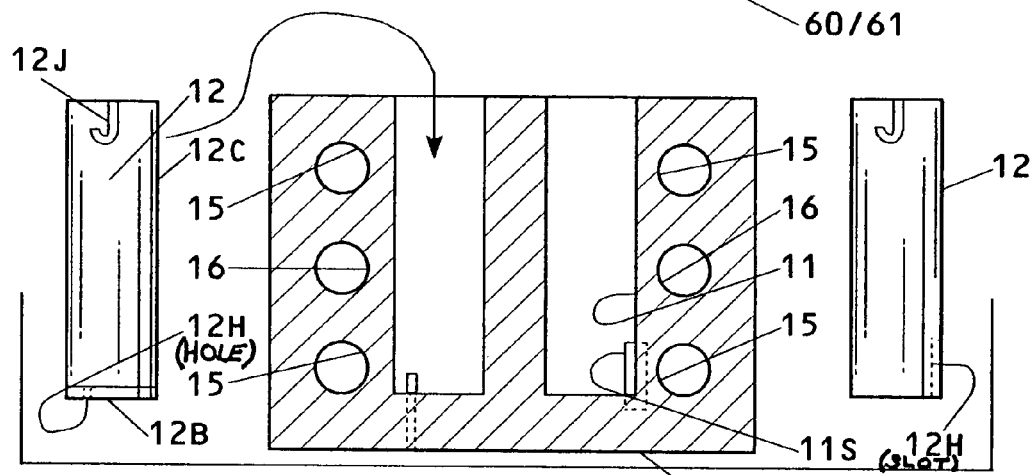
Figure 17B:
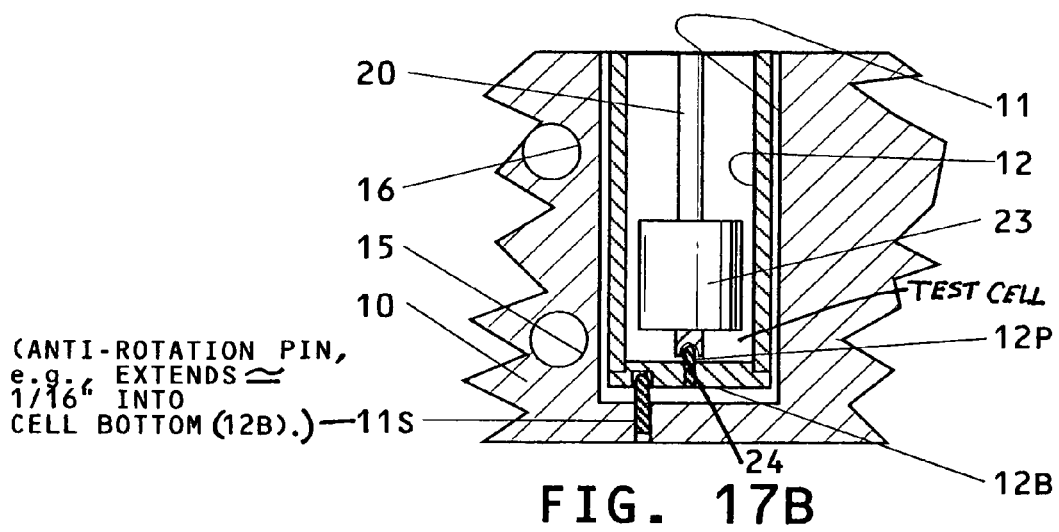

FIG. 17 shows sectional views focusing on an improvement to a block test well sleeve of the invention having a pin stop, which protrudes from the bottom of the test block, so that the sleeve is kept from rotating, depicted in exploded (A) and assembled (B) versions. Compare, FIG. 5.

The invention can be further understood by the detail below, which may be read in view of the drawings. Such is to be taken in an illustrative and not necessarily limiting sense.

As noted above, with respect to the block, the embodiments of FIGS. 1–4, 6 and 7 include center-feed moderation, with symmetrical radiating pathway direct refrigeration, and the embodiments of FIGS. 8–14 include end-feed moderation, with opposing pathway direct refrigeration. End-feed cooling moderators which appear and operate all the way in an otherwise parallel or radially symmetrical walled refrigerating pathway across the block are found in FIGS. 8–10, and end-feed cooling moderators which appear and operate part of the way in a refrigerating pathway across the block are found in FIGS. 11–14. Also, refrigerant-communication moderators are found in FIG. 1; non-refrigerating buffer space moderators are seen in FIGS. 6–14; and cascading-pathway moderation is found within the devices of FIGS. 1 and 6–14.

A passive cooling moderator may be termed a "wedge."

Although the directly refrigerated component or system can be an improvement on any of a wide variety of components or systems, to include computer processing unit (CPU) chips and other parts, superconductor substances, mechanical bearings, and so forth, and the system may have an electro-thermal chip sandwiched on a side, for example, as disclosed in the '236 application of Hildebrandt et al., preferably the directly refrigerated component or system of the invention is embodied in laboratory test equipment having a directly refrigerated block with at least one test cell for testing viscometric or rheologic properties of a sample, which may include engine oil, gear oil, automatic transmission fluid, brake fluid, hydraulic fluid, fuel, or printing ink. Preferably, the block is of a thermally conducting material such as of metal or alloy such as of aluminum, copper, gold, or steel; a plurality of test cells is present in an array, say, seven to fifteen, especially eleven in two rows; and/or the sample is oleaginous, especially of engine oil.

The directly refrigerated component or system, to include the refrigerated block, can have any suitable shape. Preferably, however, the shape, particularly for the block, is that of a cube or that of a rectangularly shaped cube, i.e., a rectangular box, especially the rectangular box.

The directly refrigerated component or system of the invention includes a refrigerating pathway, which is provided with passive cooling moderation. In passive cooling moderation, at least some moderation of cooling, and in particular of cold spots, occurs without introduction of an active agent to moderate the cooling, and cold spots as, for example, by electric heating. In other words, the makeup or structure, particularly about or in the refrigerating pathway, provides for the moderation. However, employment of an active agent to refine and assist in moderating the cooling is beneficially carried out in the practice of the present invention. Thus, for example, electric heaters may be employed along with the passive cooling moderation. When heaters of any sort are employed in a block, beneficially the heaters are adjustable, for example, as to heat output and/or to positioning within the block, notably as to the latter.

With further reference to the drawings, each of which depicts one or more components that are combined with rotors, supports, and other paraphernalia to make up a low-temperature viscometric test cell array device, as can be found in the '236 application of Hildebrandt et al., the '230 patent to Selby et al., and as is understood or otherwise known in the art, the following is noted:

Block 10, for example, of copper, is in the form of a rectangular box which includes bottom face 10B, lengthwise face 10L, top face 10T, and widthwise face 10W; and has test sleeve wells 11, say, each with an 0.865-inch diameter and a 2.51-inch depth, and optionally with a sleeve stop-engaging hole or slot 11H (FIG. 5) or as an alternative hole or slot engaging pin stop 11S (FIG. 17). The wells 11 may be provided with insertable, thermally conductive test cell sleeves 12 to hold test samples and act as stators in viscosity/rheology testing, for example, each of #304 stainless steel with a bottom 12B with an outer, circumferential cylinder-receiving shoulder, and having an overall, center thickness of 0.124 inch; cylindrical wall 12C having an outside diameter of 0.865 inches, an inside diameter of 0.748 inches, an outside height of 3.625 inches, and an inside height of 3.563 inches after insertion and silver soldering of the bottom 12B; opposing top J-slots 12J for ready insertion and removal of the sleeve 12 with a suitable tool; a carbide-tipped, 0.062-inch diameter, 0.031-inch top tip radius pin 12P centered in and standing 0.246 inch above the inside surface of the bottom 12B after it is silver soldered to a hole provided in the bottom 12B; outside pin-type stop 12S, say, at bottom, for keeping the sleeve 12 from rotating in the well 11 by engagement with the hole or slot 11H (FIG. 5), or blind pin stop hole or slot 12H on an outside part of the sleeve 12 can be for engagement with the pin stop 11S; and flat outside wall portion 12W for relieving air pressure upon insertion and withdrawal. Holes 13, 14, 15, 16 and 17 can be provided in the block 10. For example, the holes 13, say, made with a #7-drill bit 0.37 inch deep and tapped with ¼-20 threads, can be for supports for top plates for securing rotors 20; the hole 14 can be for a thermocouple temperature probe 30, for example, centered in the block 10, which may be top mount version 14T (FIGS. 1–3) that may be, for example, 0.125 inch in diameter and 1.5 inches deep, and/or which may be a side mount version 14S (FIG. 3) that may be, for example, 0.125 inch in diameter and extending lengthwise through the block 10, with the top mount version 14T with any side hole 14S absent or plugged preferred, as, among the advantages of the top mount version 14T over the side mount version 14S are that with the top mount version 14T the probe 30 is much easier to install and remove in the field, and has less of an effect in disturbing temperature linearity; the holes 15, say, 0.375 inch in diameter, extending lengthwise through the block 10, can be for insertion of heaters 40; the holes 16, say, 0.375 inch in diameter and extending lengthwise through the block 10, can serve as basic refrigeration pathways for any suitable liquid to gas type refrigerant (REF) such as of a halocarbon to include a chlorofluorocarbon, hydrohalocarbon, hydrocarbon and/or any other suitable type of refrigerant, for example, the well known R-507 refrigerant; and the holes 17, say, 0.07-inch in diameter (which may be made with a #50 drill), serve as orifices for capillary inlet tubes (FIGS. 1–3), which tubes may be, for example, of a 3-foot length and 0.026-inch inside diameter as a capillary tube coupled to a 1-foot length and 0.026-inch inside diameter inlet tube between the 3-foot length and the capillary inlet hole 17. Other holes may be present in the block 10. For instance, holes 18, 19 (FIG. 5) may be present with the hole 18, say, 8-32 tapped, centered and extending to the heater hole 15, for a set screw to hold the heaters 40 in place; and the hole 19, say, in opposing pairs 1-15/16 inches on each side of a center line (C/L), here, vertical to a lengthwise side of the block 10 and extending to the refrigeration hole 16, provide for an ability to introduce solder to hold a cooling moderator in place.

Rotor 20 can have a 6.185-inch #304 stainless steel shaft 21, with 0.560-inch long by 0.093-inch diameter top bearing 21B having an uppermost 0.046-inch radius; 0.50-inch long, 0.12-inch diameter heat-impeding neck 22 with 0.06-inch tapered lead-ins beginning 3.44 inches from the uppermost tip of the bearing 20B; cylindrical drum 23, say, of DELRIN plastic, with a 0.787-inch height and 0.669-inch outer diameter, press fit on the lower part of the shaft 21 so that its lower boundary is 0.355 inch from the bottom of the shaft 21; radial cup 24 for resting and rotating on the pin 12P, say, of solid carbide, with a 0.101-inch depth, a 0.039-inch upper radius, and flaring from the upper radius to form a 0.244-inch diameter lowermost opening; and rotor stop arms 25 centered on a line 1.31-inches from the uppermost tip of the bearing 20B. Other configurations are possible, of course.

The probe 30 can be any suitable thermocouple or thermistor, i.e., RTD, sensor. Preferably, however, the probe 30 as a top mount device is an RBGBOTA020BA480 model from WATLOW Co.

The heaters 40 can be of any suitable variety or shape, but preferably they are electric and generally cylindrically shaped. Preferably, the heaters 40 can be slid back and forth inside the holes 15 for adjustment of temperature control throughout the block 10 and test wells 11. Sizes and outputs of the heaters 40 may vary as well, and any suitable number of heaters 40 may be employed in a heater port 15. For instance, as slidable heaters 40 in the block 10, four ⅜-inch diameter by 4-inch length cartridge heaters can be employed, one per heating hole 15 and roughly centered before final adjustments therein, say, with ratings from 200–600 watts, thus, four 250-watt centered cartridge heaters, one per hole 15; as an alternative in the block 10, two centered 300-watt cartridge heaters in upper and lower holes 15 nearer a row of six wells 11, and two centered 600-watt cartridge heaters in upper and lower holes nearer a row of five wells 11; and so forth. For example, four centered 300-watt WATLOW cartridge heaters 40, one per hole 15, can be employed in the block 10. More than one heater 40, for example, two heaters, may be employed per hole 15. Also, heater(s) 40 equipped with variable power output or watt density along its length may be employed. See, e.g., FIGS. 2–4, 15 and 17.

Passive cooling moderator 60 may take any of various suitable forms. Generally, in refrigerant pathway 61, a plurality of cascade points 62 at which evaporation of the refrigerant is engendered are provided by the moderator 60, which provides for or assists in providing for the passive cooling moderation.

The passive cooling moderator 60 may be insertable. As such, it may be made of any suitable, generally thermally conducting material such as of metal or alloy such as of aluminum, copper, gold, or steel. Advantageously, in general, the insertable passive cooling moderator 60 can be made of similar material to the block 10, for example, being made of a free machining copper.

The passive cooling moderator 60 may contain moderating live space 63 (FIG. 1) and/or moderating dead space 64 (FIGS. 6–10, 13 and 14). With the live space 63, which is a preferred embodiment of the invention, auxiliary pathway 63A for the refrigerant is provided, which, for example, may surround primary pathway 63P for the refrigerant. Thus, the wedge 60 of FIGS. 1A and 1B allows the pressure of the refrigeration system to equalize from side to side, which further insures that the temperature be even throughout the evaporator, or refrigerant pathway 61. In general in refrigration, temperature is more or less directly related to pressure. With the dead space 64, is a gas filler such as air, nitrogen and/or argon, and so forth, which generally may be ambient in pressure or of a higher or lower pressure than ambient atmospheric; a liquid or solid filler; and/or a vacuum. The filler may have a lower thermal conductivity value than the moderator 60 and/or block 10. Air of generally ambient pressure at the time of manufacture is a preferred dead space filler.

The passive cooling moderator 60 can be of any suitable size and shape. For example, the moderator 60 may have length 65 of 4.00 inches; outer diameter 66 of 0.375 inches, which may be the diameter of support barrel 66B or support collar 66C; barrel outer diameter 67 of 0.255 inches; barrel inner diameter of 0.125 inch; capillary inlet port 69 of 0.07-inch diameter; and support collar angles alpha of 120-degree and beta of 90-degree values. See, FIG. 1. Compare, FIGS. 6–14.

The passive cooling moderator 60 can be intrinsic by providing the refrigeration hole(s) 16 with cascade point(s) 62 without insertable passive cooling moderator(s) 60. This can be accomplished, for example, by boring or otherwise machining the hole(s) 16 to have the desired inside dimensions as otherwise may be provided by a corresponding insertable moderator 60.

Also, a heater 40, for example, of the thin film or Kapton style, can be installed around a passive cooling moderator 60, say, prior to insertion into the block 10. Such a heater 40 basically surrounds the cold with heat to creat a buffering effect. Note, FIG. 16.

As alluded to above, the system with the block 10 and its features, to include the probe 30, heaters 40, passive cooling moderators 60, as well as the rotor 20 and the support plates, stops, weights, strings, and so forth is beneficially employed in low temperature viscometric/rheologic instrumental testing of various liquid samples, for example, engine oil, such as in the ASTM D 4684 type testing. Accordingly, incorporated herein by reference are the specifications, in their entireties, of the '236 application of Hildebrandt et al., and the '230 patent to Selby et al. Also incorporated herein by reference are the complete specifications of U.S. provisional patent application Nos. 60/269,372 filed on Feb. 16, 2001 A.D., and 60/310,768 filed on Aug. 8, 2001 A.D.

Dimensions provided hereby may be considered approximate.

The present invention is thus provided. Various features, parts, subcombinations and combinations may be employed with or without reference to other features, parts, subcombinations or combinations in the practice of the invention, and numerous adaptations and modifications can be effected within its spirit, the literal claim scope of which is particularly pointed out as follows:

We claim:

1. An article of manufacture comprising a directly refrigerated component or system in which a refrigerating pathway is provided with passive cooling moderation in a block made of a thermally conducting material, wherein the directly refrigerated component or system has the refrigerating pathway such that a refrigerant can course and cool primarily by evaporation from a liquid to a gaseous state within the passageway, and thermal conduction to include through a solid wall; and said article is a test device for rotational viscometric testing of an oleaginous fluid, with a passive cooling moderator having a moderating live space and at least two cascade points, which includes in said block:
   a plurality of vertically oriented wells into each of which can be placed a sample sleeve:
   a plurality of sample sleeves, each of which is placed into one of said wells, and each of which can receive the oleaginous fluid and a rotor;
   a heater;
   a temperature-sensing probe; and
   a refrigerant pathway, in which is positioned the passive cooling moderator;
wherein said block has a shape of a rectangularly shaped box; the heater embraces a plurality of heaters inserted into said block horizontally; the temperature-sensing probe embraces at least one such probe that is inserted into said block vertically; and the refrigerant pathway embraces a plurality of refrigerant pathways, in each of which is positioned the passive cooling moderator.

2. The article of claim 1, wherein said each of the sample sleeves is stopped from rotating in the well in which it is placed through a pin and pin-engaging hole or slot arrangement.

3. An article of manufacture comprising a directly refrigerated component or system in which a refrigerating pathway is provided with passive cooling moderation in a block made of a thermally conducting material, wherein the directly refrigerated component or system has the refrigerating pathway such that a refrigerant can course and cool primarily by evaporation from a liquid to a gaseous state within the passageway, and thermal conduction to include through a solid wall; and said article is a test device for rotational viscometric testing of an oleaginous fluid, with a passive cooling moderator having a moderating dead space and at least two cascade points, which includes in said block:
- a plurality of vertically oriented wells into each of which can be placed a sample sleeve;
- a plurality of sample sleeves, each of which is placed into one of said wells, and each of which can receive the oleaginous fluid and a rotor;
- a heater;
- a temperature-sensing probe; and
- a refrigerant pathway, in which is positioned the passive cooling moderator;

wherein said block has a shape of a rectangularly shaped box; the heater embraces a plurality of heaters inserted into said block horizontally; the temperature-sensing probe embraces at least one such probe that is inserted into said block vertically; and the refrigerant pathway embraces a plurality of refrigerant pathways, in each of which is positioned the passive cooling moderator.

4. The article of claim 3, wherein said each of the sample sleeves is stopped from rotating in the well in which it is placed through a pin and pin-engaging hole or slot arrangement.

5. An article of manufacture comprising a directly refrigerated component or system in which a refrigerating pathway is provided with passive cooling moderation, wherein said article is a test device for rotational viscometric testing of an oleaginous fluid, which article includes:
- a block made of a thermally conducting material, and having a shape of a rectangularly shaped box; and in said block:
- a plurality of vertically oriented wells into each of which can be placed a sample sleeve;
- a plurality of sample sleeves, each of which is placed into one of said wells, and each of which can receive the oleaginous fluid and a rotor;
- a heater, which embraces a plurality of heaters inserted into said block horizontally;
- a temperature-sensing probe, which embraces at least one such probe that is inserted into said block vertically; and
- a refrigerant pathway, which embraces a plurality of refrigerant pathways, in each of which is positioned a passive cooling moderator to provide for.

6. The article of claim 5, with a passive cooling moderator having a moderating live space and at least two cascade points.

7. The article of claim 6, wherein said each of the sample sleeves is stopped from rotating in the well in which it is placed through a pin and pin-engaging hole or slot arrangement.

8. The article of claim 5, with a passive cooling moderator having a moderating dead space and at least two cascade points.

9. The article of claim 8, wherein said each of the sample sleeves is stopped from rotating in the well in which it is placed through a pin and pin-engaging hole or slot arrangement.

10. The article of claim 5, wherein said each of the sample sleeves is stopped from rotating in the well in which it is placed through a pin and pin-engaging hole or slot arrangement.

\* \* \* \* \*